United States Patent [19]

Kanayama

[11] Patent Number: 4,656,294

[45] Date of Patent: Apr. 7, 1987

[54] POLYGLYCIDYL ETHERS AND A PROCESS FOR PRODUCING THE SAME

[75] Inventor: Kaoru Kanayama, Ibaraki, Japan

[73] Assignee: Mitsubishi Petrochemical Co., Ltd., Tokyo, Japan

[21] Appl. No.: 630,817

[22] Filed: Jul. 13, 1984

[30] Foreign Application Priority Data

Jul. 15, 1983 [JP] Japan .................................. 58-128992
Jun. 11, 1984 [JP] Japan .................................. 59-119612

[51] Int. Cl.$^4$ ............................................ C07D 319/00
[52] U.S. Cl. ........................................ 549/335; 528/96
[58] Field of Search .......................................... 549/335

[56] References Cited

U.S. PATENT DOCUMENTS 3,347,871 10/1967 Harding .............................. 549/335
3,388,098 6/1968 Harding .............................. 549/335

Primary Examiner—Dolph H. Torrence
Attorney, Agent, or Firm—Oblon, Fisher, Spivak, McClelland & Maier

[57] ABSTRACT

A process for producing a polyglycidyl ether which comprises reacting a mixture of 4-oxy-3-methoxybenzaldehyde and 4-oxybenzaldehyde in the molar ratio of 5/95 to 95/5 with pentaerythritol to give a bisphenol having a spiroacetal ring, and further reacting the bisphenol with epihalohydrin or β-methylepihalohydrin is disclosed. The polyglycidyl ether obtained has excellent solubility in solvents, and the cured product obtained therefrom has excellent elongation, modulus of elasticity, impact resistance, and heat resistance.

11 Claims, No Drawings

POLYGLYCIDYL ETHERS AND A PROCESS FOR PRODUCING THE SAME

FIELD OF THE INVENTION

The present invention relates to a process for producing a polyglycidyl ether having a spiroacetal ring which has an excellent solubility and provides a cured product having balanced elongation and stiffness, excellent heat resistance and excellent impact resistance.

The polyglycidyl ether obtained by the process according to the present invention is useful as a matrix resin for CFRP (Carbon Fiber Reinforced Plastics), a sealing material for electronics parts, a casting material, a laminate material, a paint binder and the like.

BACKGROUND OF THE INVENTION

Epoxy resins have excellent heat resistance, electrical insulation, chemical resistance and mechanical properties, and are widely used in the fields of, for example, paints, adhesives, sealing materials, and structural materials.

Recently, epoxy-carbon fiber composite materials (CFRP) have come into use as structural materials for aircraft, spacecraft, trains, automobiles, and other vehicles, and as sporting goods such as golf club shafts, fishing rods, and skis, because of its mechanical strength and modulus of elasticity comparable to or superior to metals and its light weight.

The polyepoxy compounds used as the matrix resin for CFRP include diglycidyl ether of bisphenol A (e.g., Epikote 828 and Epikote 1004, products of Yuka Shell Epoxy Co., Ltd.), polyepoxide of aminophenol (e.g., ELM-120, a product of Sumitomo Chemical Co., Ltd.), tetraepoxide of methylenedianiline (e.g., YH-434, a product of Toto Kasei Co., Ltd.), cresol novolak polyepoxide (e.g., Epikote 154, a product of Yuka Shell Epoxy Co., Ltd.), and o-cresol novolak epoxide (e.g., EOCN 104S, a product of Nippon Kayaku Co., Ltd.).

The cured products obtained from these polyepoxy compounds have sufficient heat resistance, but they still need improvements in flexibility and impact resistance when used as CFRP.

It is known that a polyepoxy compound having a spiroacetal ring provides a cured product having good flexibility. For example, U.S. Pat. No. 3,128,255 discloses a polyepoxy compound of the formula

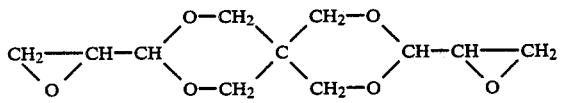

The cured product obtained from this compound has a heat distortion temperature of 147° to 170° C., and lacks heat resistance when used as CFRP resin.

U.S. Pat. Nos. 3,347,871 and 3,388,098 also disclose a polyepoxy compound of the formula

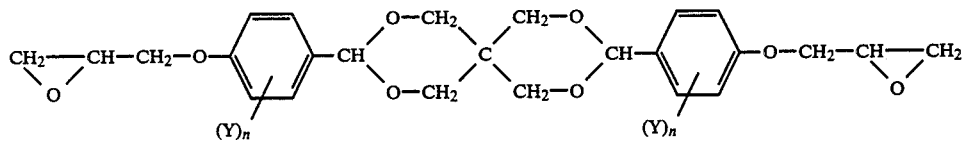

wherein Y is H, Cl or CH₃, and n is an integer of 0 to 2, which is obtained by (A) reacting pentaerythritol with a monohydric phenol having an aldehyde group at the para position with respect to the phenolic hydroxyl group, and (B) reacting the resulting dihydric phenol with epichlorohydrin.

This polyepoxy compound provides a cured product having excellent heat resistance and impact resistance but needs improvements in flexibility. In addition, the compound has poor solubility in conventional solvents such as acetone, methyl ethyl ketone, methyl isobutyl ketone, toluene, ethyl acetate, and tetrahydrofuran. Thus, it is not suitable for prepreg and paint applications in which solvent dilution is necessary.

SUMMARY OF THE INVENTION

The present inventor founds that when 4-oxy-3-methoxybenzaldehyde and 4-oxybenzaldehyde are used together as the monohydric phenol in the above-mentioned U.S. Pat. No. 3,347,871, there is obtained a polyglycidyl ether which is readily soluble in conventional solvents and provides a cured product having excellent heat resistance, flexibility, and elongation-stiffness balance. The present invention was completed based on this finding.

Accordingly, an object of the present invention is to provide a process for producing a polyglycidyl ether which comprises reacting a mixture of 4-oxy-3-methoxybenzaldehyde and 4-oxybenzaldehyde in the molar ratio of 5/95 to 95/5 with pentaerythritol to give a bisphenol having a spiroacetal ring, and further reacting the bisphenol with epihalohydrin or β-methylepihalohydrin.

DETAILED DESCRIPTION OF THE INVENTION

The bisphenol mixture having a spiroacetal ring used in the present invention is easily produced by dehydrocondensation of a mixture of 4-oxy-3-methoxybenzaldehyde (5 to 95 mol%, preferably 20 to 80 mol%) and 4-oxybenzaldehyde (95 to 5 mol%, preferably 80 to 20 mol%) with pentaerythritol under heating at 40° to 200° C., preferably 80° to 150° C., in the presence of a catalyst. The raw materials are generally charged in such a ratio that the amount of aldehyde is a stoichiometric amount per 1 mol of pentaerythritol but an excess amount of aldehyde may be used.

It is preferred that the water formed by condensation be continuously removed by azeotropic distillation with an appropriate solvent. The solvent for azeotropic distillation includes aromatic hydrocarbons such as benzene, toluene, and xylene which are economical. Those may be used in combination with any one of N,N-dimethylformamide, N,N-dimethylacetamide, N-methylpyrrolidone, tetrahydrofuran, dioxane, and dimethylsulfoxide which are good solvents for the pentaerythritol.

The catalyst used for condensation includes p-toluenesulfonic acid, oxalic acid, zinc acetate, hydrochloric acid, and sulfuric acid which are conventionally used in dehydrocondensation. Of those catalysts, p-toluenesulfonic acid is preferred.

In general, when 4-oxy-3-methoxybenzaldehyde is used in a large amount, the resulting polyglycidyl ether is easily soluble in solvents and the elongation of the cured product obtained therefrom is improved. 4-Oxybenzaldehyde improves the heat resistance and mechanical strength of the cured product of the resulting polyglycidyl ether.

The bisphenol mixture is difficult to separate. Judging from the raw materials used, it is believed that the mixture is composed of bisphenols represented by the formulae (I) to (III):

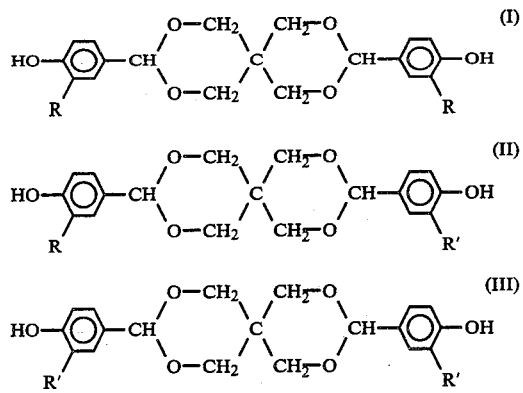

wherein R is hydrogen and R' is a methoxy group.

The dihydric bisphenol mixture obtained by the above-described reaction is then reacted with epihalohydrin or β-methylepihalohydrin (hereinafter, referred to as "epihalohydrin", for brevity) to give polyglycidyl ether. This reaction can be accomplished by any conventional epoxidizing processes as exemplified below.

(1) One-stage process in which the bisphenol mixture is reacted with excess epihalohydrin in the presence of an alkali metal hydroxide. In this process, the addition reaction between bisphenol and epihalohydrin and the ring closure reaction to form an epoxy ring take place simultaneously.

(2) Two-stage process in which the addition reaction between the bisphenol mixture and excess epihalohydrin is performed in the presence of a phosphonium salt or quaternary ammonium salt, and then an alkali metal hydroxide is added for ring closure reaction.

(3) Solvent process in which the bisphenol mixture, excess epihalohydrin, a solvent such as alcohol, and an aqueous solution of alkali metal hydroxide are reacted together at room temperature to 80° C. The solvent is used to accelerate the reaction. In this process, the addition reaction and ring closure reaction take place simultaneously.

The polyglycidyl ethers obtained by these processes differ in molecular weight distribution. It increases in the order of (1), (2), and (3). A proper process should be selected according to the intended use.

In the case of epoxidizing process (1), the reaction is conducted at 60° to 150° C., preferably 80° to 120° C. Epihalohydrin is added in an amount of 2 to 20 mol, preferably 8 to 12 mol, per mol of the bisphenol mixture having a spiroacetal ring. The alkali metal hydroxide is added in an amount of at least 1 mol, preferably 1.05 to 1.5 mol, per mol of hydroxyl group in the bisphenol mixture.

In the case of epoxidizing process (2), the addition reaction in the first stage is conducted at 40° to 150° C., preferably 70° to 140° C., and the ring closure reaction in the second stage is conducted at 20° to 150° C., preferably 40° to 80° C. The catalyst is used in an amount of 0.1 to 5 mol% based on the bisphenol mixture. Epihalohydrin and alkali metal hydroxide are added in the same amounts as in the one-stage process.

In the case of epoxidizing process (3), the solvent is used in an amount of 0.2 to 5.0 mol%, preferably 0.5 to 2.0 mol%, based on epihalohydrin, and the reaction temperature is room temperature to 80° C.

The reaction in the one-stage process and the ring closure reaction in the two-stage process may be carried out while discharging continuously the water formed by the reaction by azeotropic distillation with epihalohydrin under normal pressure or reduced pressure (50 to 200 mmHg).

When these reactions are completed, the reaction liquid is filtered using a filter aid such as zeolite to remove the salt formed as a by-product, and then unreacted epihalohydrin is recovered under reduced pressure to give the desired product. Alternatively, the reaction liquid is subjected to distillation under reduced pressure to recover unreacted epihalohydrin, and the residues are dissolved in an organic solvent such as methyl isobutyl ketone and toluene which are difficultly soluble in water. The resulting solution is brought into contact with water or hot water so that sodium chloride and other inorganic impurities are dissolved in the water phase. Finally, the organic solvent is distilled away and the product is purified.

Epihalohydrin used as the raw material includes epichlorohydrin, epibromohydrin, β-methylepichlorohydrin, and β-methylepibromohydrin.

The alkali metal hydroxide includes potassium hydroxide and sodium hydroxide.

The catalyst used for the addition reaction in the two-stage process includes, for example, quaternary ammonium salt and phosphite. Examples of quaternary ammonium salt include tetramethyl ammonium chloride, tetraethyl ammonium bromide, triethylmethyl ammonium chloride, tetraethyl ammonium iodide, and cetyltriethyl ammonium bromide. Examples of phosphite include triphenyl phosphonium halide (e.g., iodide, bromide, and chloride), triphenylethyl phosphonium, and diethyl phosphate. The preferred catalyst is tetramethyl ammonium chloride or tetraethyl ammonium bromide.

The polyglycidyl ether thus obtained is a mixture of polyglycidyl ethers represented by the formulae (IV) to (VI):

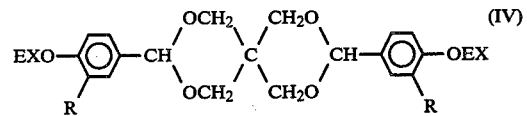

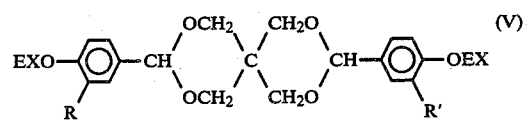

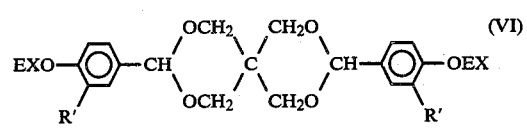

wherein R is hydrogen, R' is a methoxy group, and EX is

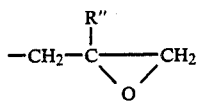

wherein R" is hydrogen or a methyl group.

The polyglycidyl ether mixture may contain less than 40 wt% of polymers represented by the following formulae (VII) to (IX), depending on the reaction and purification conditions.

The polyglycidyl ether obtained according to this invention has a comparatively low softening point and provides a cured product which has balanced elongation and modulus of elasticity. Thus, it is useful as a matrix resin for CFRP and is also useful as a prepreg varnish because of its solubility in acetone, methyl ethyl ketone, methyl isobutyl ketone, toluene, ethyl acetate, and methylene chloride.

Further embodiment of the present invention is to further improve the impact resistance of the specific polyglycidyl ether obtained above.

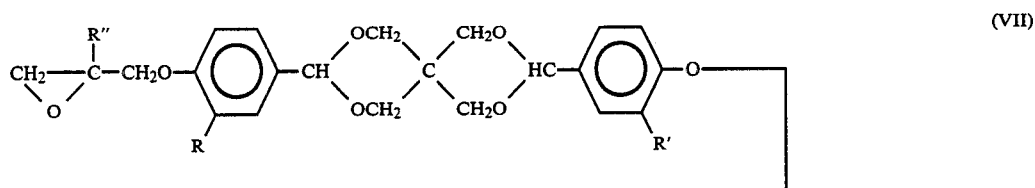

(VII)

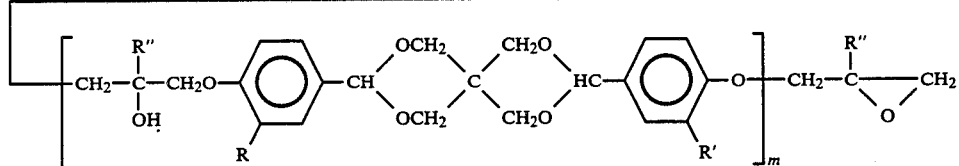

(VIII)

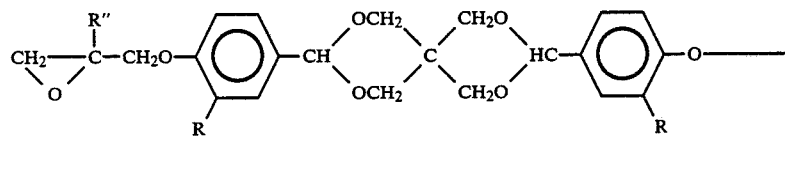

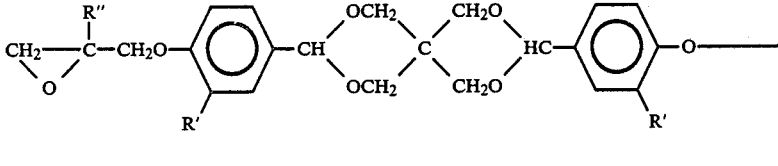

(IX)

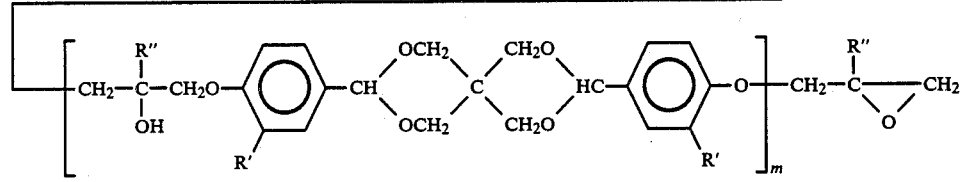

wherein R is hydrogen, R' is a methoxy group, R" is hydrogen or a methyl group, and m is an integer of 1 to 5.

When the polyglycidyl ether obtained is a diglycidyl ether represented by the formula (X)

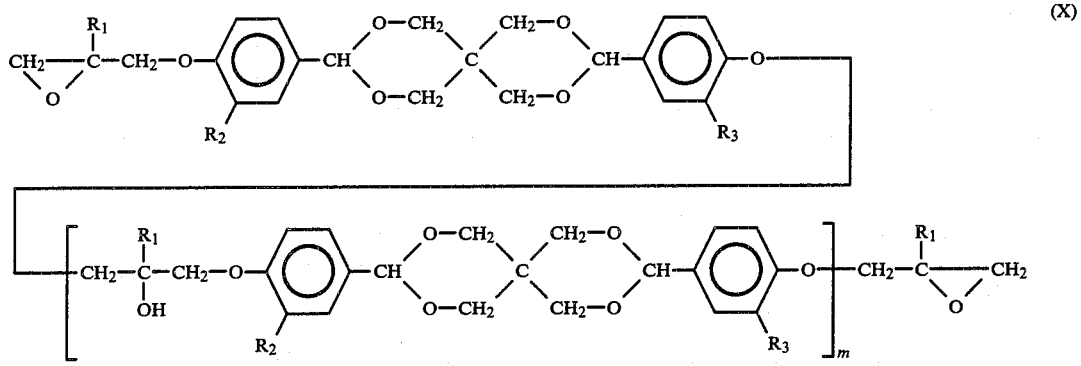

wherein $R_1$ is H or $CH_3$, $R_2$ and $R_3$ are independently hydrogen or a methoxy group, and m is 0 to 1, the diglycidyl ether is further reacted with a bisphenol represented by the formula (XI)

HO—Ar—OH      (XI)

wherein Ar is

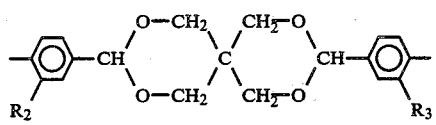

wherein $R_2$ and $R_3$ are the same as defined above,

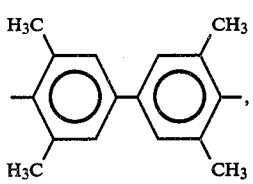

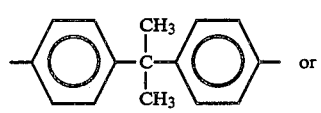  or

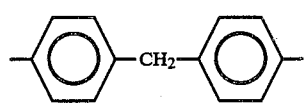

to obtain a polyglycidyl ether having a further improved impact resistance represented by the formula (XII)

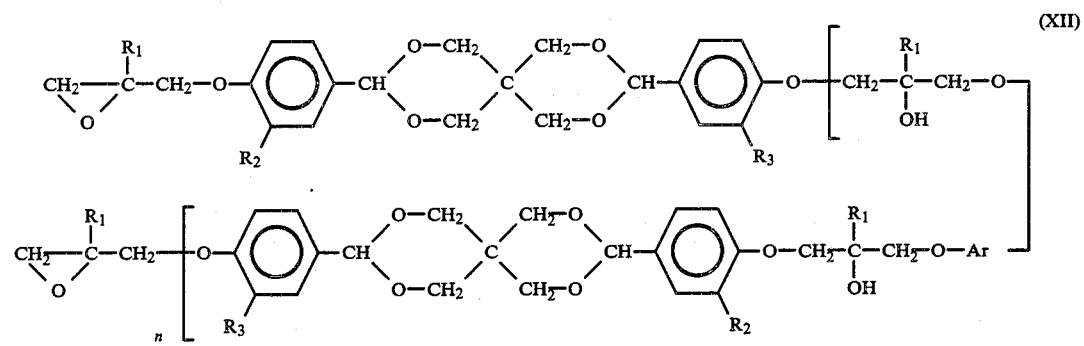

wherein $R_1$, $R_2$, $R_3$ and Ar are the same as defined above, $R_2$ and $R_3$ are not simultaneously hydrogen or a methoxy group, and n is 0 or an integer of 1 to 20.

The methoxy group content in the formula (XII) is 5 to 95%, preferably 20 to 80%.

The diglycidyl ether of the formula (X) is a low molecular weight epoxy compound which is obtained by reacting the bisphenol of the formulae (XI) wherein Ar is

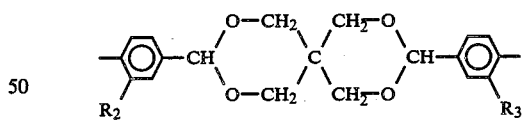

(wherein $R_2$ and $R_3$ are the same as defined above and the methoxy group content in $R_2$ and $R_3$ is 5 to 95%) and epihalohydrin or β-methylepihalohydrin in the presence of caustic soda or alternatively reacting those in the presence of a catalyst such as phosphonium salt or tetramethylammonium bromide to obtain halohydrin ether and subjecting it to a ring closure reaction.

The meaning of m=0 to 1 is that the epoxy resin generally produced comprises mainly the compound where m=0 but contains slightly the compounds where m=1, 2 and the like, and the epoxy resin of the formula (X) is the compound where the average value of m is 0 to 1.

Of the bisphenols of the formula (XI), the bisphenol where Ar is

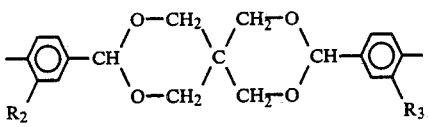

wherein $R_2$ and $R_3$ are the same as defined above is easily produced by dehydrocondensation of a mixture of 4-oxy-3-methoxybenzaldehyde (5 to 95 mol%) and 4-oxybenzaldehyde (95 to 5 mol%) with pentaerythritol under heating at 40° to 200° C., preferably 80° to 150° C., in the presence of an acidic catalyst. The raw materials are generally charged in such a ratio that the amount of aldehyde is a stoichiometric amount (2 mols) per 1 mol of pentaerythritol but an excess amount of aldehyde may be used.

It is preferred that the water formed by condensation be continuously removed by azeotropic distillation with an appropriate solvent.

The solvent for azeotropic distillation includes aromatic hydrocarbons such as benzene, toluene, and xylene which are economical. Those may be used in combination with any one of N,N-dimethylformamide, N,N-dimethylacetamide, N-methylpyrrolidone, tetrahydrofuran, dioxane, and dimethylsulfoxide which are good solvents for the aldehydes.

The catalyst used for condensation includes p-toluenesulfonic acid, oxalic acid, zinc acetate, hydrochloric acid, and sulfuric acid which are conventionally used in dehydrocondensation. Of those catalysts, p-toluenesulfonic acid is preferred.

The conditions for producing a polyepoxy compound having a spiroacetal ring by reacting the bisphenol of the formula (XI) and the diglycidyl ether of the formula (X) are explained in detail below.

One equivalent of diglycidyl ether of the formula (X) is reacted with 0.05 to 1.0 equivalent of bisphenol, preferably 0.1 to 0.8 equivalent of bisphenol of the formula (XI), in the presence of a catalyst at 80° to 230° C., preferably 150° to 230° C., for 0.1 to 10 hours, preferably 0.3 to 6 hours, while stirring.

The catalyst used for the reaction includes, for example, quaternary ammonium salt, phosphite, and phosphonium. Examples of quaternary ammonium salt include tetramethyl ammonium chloride, tetraethyl ammonium bromide, triethylmethyl ammonium chloride, tetraethyl ammonium iodide, and cetyltriethyl ammonium bromide. Examples of phosphonium include triphenyl phosphonium halide (e.g., iodide, bromide, and chloride), triphenylethyl phosphonium, and diethyl phosphate and phosphonate.

The reaction can be conducted in the presence of a solvent. The solvent used is not particularly restricted so long as it is inert to and soluble in the starting epoxy compound and bisphenol. Examples of the solvent ketones such as methyl ethyl ketone, methyl isobutyl ketone, acetophenone or benzophenone; aromatic hydrocarbons such as benzene, toluene or xylene; halogenated hydrocarbons such as 1,2-dichloroethane, chlorobenzene or dichlorobenzene; glymes such as ethyleneglycol dimethyl ether or diethyleneglycol dimethyl ether; cellosolves such as ethyl cellosolve or butyl cellosolve; non-protonic polar solvents such as N,N'-dimethyl formamide, N,N'-dimethyl acetomamide or dimethyl sulfoxide.

If the proportion of the bisphenol of the formula (XI) to the diglycidyl ether (X) exceeds 0.8 equivalent, the molecular weight of the polyepoxy compound obtained increases, resulting in the problem of deteriorating the operability due to increase of a melt viscosity. On the other hand, the proportion thereof is lower than 0.05 equivalent, the molecular weight of the epoxy compound obtained is low and the effect of improving the impact resistance cannot be obtained.

The polyepoxy compound obtained by the reaction is solid at normal temperature (e.g., 20° C.) and has a molecular weight of about 600 to 2,000 and epoxy equivalents of 200 to 600.

The polyepoxy compound having a spiroacetal ring has excellent impact resistance and elongation and is useful as a reinforced plastic. Further, the polyepoxy compound is soluble in acetone, methyl ethyl ketone, methyl isobutyl ketone, toluene, ethyl acetate, methylene chloride and the like and therefore is useful as a raw material of varnish for prepreg.

The polyglycidyl ether obtained by the processes of the present invention can be used alone or in combination with other epoxy compounds in the areas where epoxy resins are used. Upon curing (crosslinking) with a proper hardener, the difunctional polyglycidyl ether mixture used alone or in combination with other epoxy compounds provides a cured product having excellent heat resistance, flexibility, and impact resistance. The other epoxy compound to be combined is not specifically limited and various epoxy compounds can be used according to the intended use. Examples of such epoxy compounds include polyglycidyl ethers such as bisphenol A and bromobisphenol A, polyglycidyl esters of phthalic acid or cyclohexane dicarboxylic acid, polyglycidylamine of aniline or methylene dianiline, epoxy compounds of aminophenol, and phenol novolak and cresol novolak.

The polyglycidyl ether mixture can be cured with conventional various hardeners which are used for epoxy resins. The examples thereof include a aliphatic amines, aromatic amines, heterocyclic amines, Lewis acid or salt thereof such as boron trifluoride, organic acids, organic acid anhydrides, urea and derivatives thereof, and polymercaptans. Typical examples include aromatic amines such as diaminodiphenylmethane, diaminodiphenylsulfone, and 2,4-diamino-m-xylene; imidazole, imidazole substitute and a salt thereof with an organic acid, such as 2-methylimidazole, 2,4,5-triphenylimidazole, and 1-cyanoethyl-2-methylimidazole; organic carboxylic acid such as fumaric acid, trimellitic acid, and hexahydrophthalic acid; organic acid anhydride such as phthalic anhydride, endomethylenetetrahydrophthalic anhydride, hexahydrophthalic anhydride; urea derivatives such as dicyandiamide, melamine, and guanamine; aliphatic polyamines such as triethylenetetramine, diethylenetriamine, xylylenediamine, and isophoronediamine; and adducts of a polyamine and an epoxy compound (e.g., ethylene oxide and propylene oxide) or an acrylic compound (e.g., acrylonitrile and acrylic acid).

The polyglycidyl ether can contain, in addition to a hardener, plasticizer, organic solvent, reactive diluent, extender, filler, reinforcement, pigment, flame retardant, thickener, flexibilizer, and other additives, if desired and necessary.

The polyglycidyl ether obtained according to the process of this invention provides a cured product of epoxy resin which has excellent balance between elongation and modulus of elasticity, impact strength, and heat resistance. It is useful as a matrix resin for CFRP, a sealing compound for electronics parts, a casting material, a laminating material, and paint.

The invention is now described in more detail with reference to the following examples, which are not intended to limit the scope of this invention.

PRODUCTION EXAMPLE 1

Into a one liter four-necked flask equipped with a thermometer, nitrogen inlet, stirrer, and water separator were charged 76 g (0.5 mol) of 4-oxy-3-methoxybenzaldehyde (vanilin), 61 g (0.5 mol) of 4-hydroxybenzaldehyde, 68 g of pentaerythritol, 30 g of p-toluenesulfonic acid, 500 ml of toluene, and 150 ml of N,N-dimethylformamide. The reactants were heated at 120° C. under nitrogen stream to carry out dehydrocondensation. The water formed by the reaction was removed continuously by azeotropic distillation with toluene. When the distilled water reached a theoretical quantity (18 ml), the reaction was terminated.

After the completion of the reaction, the solution of the product was poured into 5 liters of water. The crystals which had separated were filtered off and then dried. Thus, 147.7 g (yield: 79.0%) of light red crystals of bisphenol having a spiroacetal ring was obtained. The melting point of the crystals was 189° to 204° C. It was found by liquid chromatography that the crystals were a mixture of compounds represented by the following formula (X)

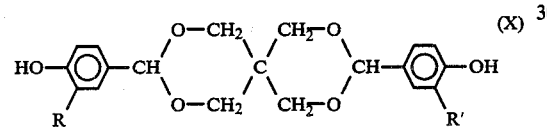

The mixture was composed of 25% of the compound of formula (X) in which $R=R'=H$, 25% of the compound of formula (X) in which $R=R'=OCH_3$, and 50% of the compound of formula (X) in which $R=H$ and $R'=OCH_3$.

PRODUCTION EXAMPLE 2

Production Example 1 was repeated except that the amount of vanilin was charged to 38 g (0.25 mol) and the amount of p-hydroxybenzaldehyde was changed to 91.5 g (0.75 mol). 133.4 g (yield: 74.3%) of light redbrown crystals of bisphenol having a spiroacetal ring was obtained.

The melting point of the crystals was 206° to 221° C. It was found by liquid chromatography that the crystals were a mixture composed of 54.2% of the compound of formula (X) in which $R=R'=H$, 8.3% of the compound of formula (X) in which $R=R'=OCH_3$, and 37.5% of the compound of formula (X) in which $R=H$ and $R'=OCH_3$.

PRODUCTION EXAMPLE 3

Production Example 1 was repeated except that the amount of vanilin was changed to 114 g (0.75 mol) and the amount of p-hydroxybenzaldehyde was changed to 30.5 g (0.25 mol). 137.1 g (yield: 70.5%) of light brown crystals of bisphenol having a spiroacetal ring was obtained (Melting point: 182° to 201° C.). It was found by liquid chromatography that the crystals were a mixture composed of 8.0% of the compound of formula (X) in which $R=R'=H$, 56.7% of the compound of formula (X) in which $R=R'=OCH_3$, and 35.3% of the compound of formula (X) in which $R=H$ and $R'=OCH_3$.

PRODUCTION EXAMPLE 4

Production Example 1 was repeated except that the vanilin (76 g) and p-hydroxybenzaldehyde (61 g) were replaced by 122 g (1.0 mol) of p-hydroxybenzaldehyde. White powder of 3,9-bis(p-hydroxyphenyl)-2,4,8,10-tetraoxaspiro[5.5]undecane was obtained (Melting point: 251° to 253° C.).

PRODUCTION EXAMPLE 5

Production Example 4 was repeated except that the p-hydroxybenzaldehyde (122 g) was replaced by 150 g (1 mol) of 3-chloro-4-hydroxybenzaldehyde. 3,9-bis(p-chlorohydroxyphenyl)-2,4,8,10-tetraoxaspiro[5.5]undecane was obtained.

PRODUCTION EXAMPLE 6

Production Example 4 was repeated except that the p-hydroxybenzaldehyde (122 g) was replaced by 133 g (1 mol) of 3-methyl-4-hydroxybenzaldehyde. 3,9-bis(p-2-methylhydroxyphenyl)-2,4,8,10-tetraoxaspiro[5.5]undecane was obtained.

PRODUCTION EXAMPLE 7

Production Example 4 was repeated except that the p-hydroxybenzaldehyde (122 g) was replaced by 122 g (1 mol) of vanilin. 132.1 g of white powder of 3,9-bis(4-oxy-3-methoxyphenyl)-2,4,8,10-tetraoxaspiro[5.5]undecane was obtained. Melting point: 175° C.

EXAMPLE 1

Into a one liter three-necked flask equipped with a thermometer, condenser, and stirrer were charged 187 g (0.5 mol) of bisphenol having a spiroacetal ring which had been obtained in the above-mentioned Production Example 1, 462.5 g (5.0 mol) of epichlorohydrin, and 40 g of tetramethylammonium bromide. Reaction was carried out under reflux (117° C.) for 2 hours.

The reaction solution was cooled to 60° C. A water separator was attached to the flask. 42 g of sodium hydroxide (1.05 mol) was added. Ring closure reaction was carried out under reduced pressure (150 to 100 mmHg). The water formed by the reaction was removed continuously by azeotropic distillation with epichlorohydrin. When the amount of removed water reached 18 ml, the reaction was terminated.

Unreacted epichlorohydrin was removed under reduced pressure of 0.1 to 50 mmHg at 60° to 110° C. One liter of methyl isobutyl ketone was added to change the product into a slurry. The slurry product was washed thoroughly with 500 ml of water to remove sodium chloride formed as a by-product.

Methyl isobutyl ketone was distilled away under reduced pressure using a rotary evaporator. Thus 228 g of light yellow solid having an epoxy equivalent of 280 and a softening point of 72° to 78° C. was obtained.

EXAMPLE 2

The epoxidizing reaction was carried out in the same manner as in Example 1 except that the bisphenol was replaced by 179.5 g of bisphenol obtained in the above-mentioned Production Example 2. 212 g of light yellow solid having an epoxy equivalent of 260 and a softening point of 75° to 85° C. was obtained.

EXAMPLE 3

The epoxidizing reaction was carried out in the same manner as in Example 1 except that the bisphenol was replaced by 194.5 g of bisphenol obtained in the abovementioned Production Example 3. 223 g of light yellow solid having an epoxy equivalent of 292 and a softening point of 61° to 70° C. was obtained.

COMPARATIVE EXAMPLES 1 TO 4

Polyglycidyl ethers as shown in Table 1 were produced in the same manner as in Example 1 except that 0.5 mol each of bisphenols obtained in Production Examples 4 to 7 was used.

Solubility Test:

5 parts by weight of each polyglycidyl ether obtained in Examples 1 to 3 and Comparative Examples 1 to 4 was mixed with 95 parts by weight of various solvents. For comparison, "Epikote 828" (diglycidyl ether of bisphenol A; epoxy equivalent: about 186; a product of Yuka Shell Epoxy Co., Ltd.) was also treated. The results obtained are shown in Table 1.

TABLE 1

|  | Examples | | | Comparative Examples | | | | Epikote 828 |
|---|---|---|---|---|---|---|---|---|
|  | 1 | 2 | 3 | 1* | 2* | 3* | 4 |  |
| Monohydric phenol as raw material | See (1) | See (2) | See (3) | See (4) | See (5) | See (6) | See (7) | — |
| Epoxy equivalent | 280 | 260 | 292 | 242 | 278 | 256 | 284 | 186 |
| Softening point (°C.) | 72–78 | 75–85 | 61–70 | 158 | 170 | 85–90 | 65–72 | liquid |
| Solubility |  |  |  |  |  |  |  |  |
| Acetone | S | S | S | IS | IS | PS | S | S |
| Methyl ethyl ketone | S | S | S | IS | IS | PS | S | S |
| Methyl isobutyl ketone | S | S | S | IS | IS | IS | S | S |
| Toluene | S | S | S | IS | IS | IS | S | S |
| Ethyl acetate | S | S | S | IS | IS | IS | S | S |
| Tetrahydrofuran | S | S | S | PIS | PIS | S | S | S |
| Methanol | IS | IS | IS | IS | IS | IS | IS | IS |

S Soluble
IS Insoluble
PS Partly soluble
PIS Partly insoluble
*Compounds disclosed in Example of USP 3,388,098.

(1) 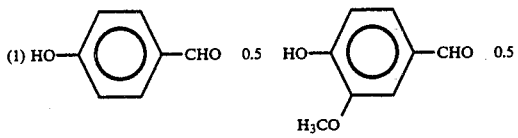

(2) 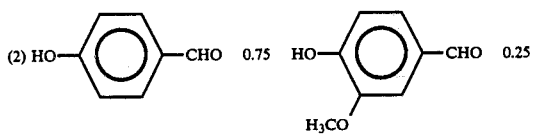

(3) 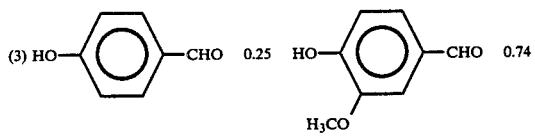

(4) 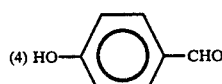

(5) 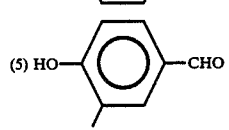

(6) 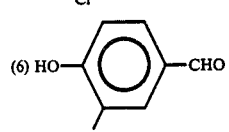

(7) 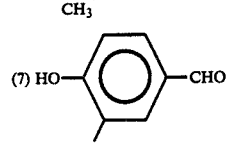

APPLICATION EXAMPLES

Production of Cured Products:

100 parts by weight of each of polyglycidyl ethers obtained in Examples 1 to 3 and Comparative Examples 1 and 4 and "Epikote 828" was blended with an equivalent of methyl nadic anhydride (a hardener made by Nippon Kayaku Co., Ltd.) and 1 part by weight of 2-ethyl-4-methylimidazole (a cured catalyst made by Shikoku Kasei Co., Ltd.).

After melt kneading at 170° C. and complete deaeration, the mixture was cast into a mold. Precuring was carried out at 100° C. for 3 hours, and postcuring was carried out at 200° C. for 6 hours. Thus, a cured product having a length of 150 mm, a width of 150 mm and a thickness of 3 mm was obtained. The physical properties of the cured products are shown in Table 2.

The same experiment as above was conducted except that methyl nadic anhydride was replaced by diaminodiphenylsulfone, mixing was performed at 180° C., precuring was performed at 180° C. for 1 hour and postcuring was performed at 190° C. for 4 hours. The physical properties of the cured products are shown in Table 3.

PRODUCTION EXAMPLE 9

The same starting materials as in Example 1 except that the bisphenol was replaced by 172 g of bisphenol obtained in Production Example 4 were charged and addition reaction was carried out in an oil bath at 117° C. for 2 hours.

The temperature of the reaction system was cooled to 60 C. A water separator was attached to the flask. 42 g (1.05 mol) of solid sodium hydroxide was added.

Ring closure reaction was carried out by reducing the pressure in the reaction system to 100 mmHg, removing water formed by means of azeotropic distillation with epichlorohydrin and continuously recycling the separated epichlorohydrin to the reaction system for 2 hours.

After completion of the reaction, the reaction prod-

TABLE 2

| | Application Examples | | | Referencial Examples | | |
|---|---|---|---|---|---|---|
| Composition (parts by weight): | | | | | | |
| Polyglycidyl ether | 100 (Example 1) | 100 (Example 2) | 100 (Example 3) | 100 (Comparative Example 1) | 100 (Comparative Example 4) | 100 Epikote 828 |
| Methyl nadic anhydride | 61 | 66 | 59 | 70 | 60 | 90 |
| 2-Ethyl-4-methylimidazole | 1 | 1 | 1 | 1 | 1 | 1 |
| Properties of cured product: | | | | | | |
| Heat distortion temperature (°C.)* | 194 | 205 | 189 | 208 | 179 | 166 |
| Flexural strength (kg/mm$^2$)** | 13.3 | 14.1 | 12.8 | 11.0 | 11.3 | 12.9 |
| Flexural modulus (kg/mm$^2$) | 400 | 430 | 380 | 270 | 392 | 280 |
| Izod impact strength (notched)** (kg-cm/cm) | 5.5 | 6.3 | 6.0 | 3.1 | 3.5 | 2.0 |

Test method:
*ASTM D-648
**JIS K-6911

TABLE 3

| | Application Examples | | | Referencial Examples | | |
|---|---|---|---|---|---|---|
| Composition (parts by weight): | | | | | | |
| Polyglycidyl ether | 100 (Example 1) | 100 (Example 2) | 100 (Example 3) | 100 (Comparative Example 1) | 100 (Comparative Example 4) | 100 Epikot 828 |
| 4,4'-Diaminodiphenylsulfone | 22.1 | 23.9 | 21.2 | 24.2 | 21.9 | 32.7 |
| Properties of cured product: | | | | | | |
| Heat distortion temperature (°C.)* | 210 | 217 | 204 | 220 | 190 | 191 |
| Flexural strength (kg/mm$^2$)** | 11.2 | 10.3 | 10.5 | 9.5 | 14.2 | 12.6 |
| Flexural modulus (kg/mm$^2$)** | 350 | 370 | 300 | 370 | 320 | 290 |
| Izod impact strength (notched)** (kg · cm/cm) | 4.3 | 4.0 | 4.9 | 3.2 | 4.1 | 2.4 |
| Tensile strength (kg/mm$^2$)** | 8.8 | 7.6 | 8.5 | 7.5 | 10.3 | 7.6 |
| Tensile modulus (kg/mm$^2$)** | 530 | 470 | 440 | 390 | 260 | 270 |
| Tensile elongation (%)** | 6.0 | 4.7 | 5.5 | 2.0 | 4.9 | 2.8 |
| Water absorption (%)*** | 1.7 | 1.6 | 1.7 | 1.6 | 1.6 | 1.5 |

Test method:
*ASTM D-648
**JIS K-6911
***Weight increase after dipping in boiling water for 10 hours.

It can be understood from the above results that polyglycidyl ether of this invention has an excellent solubility in solvents, and the cured product obtained therefrom has excellent elongation, modulus of elasticity, impact resistance, and heat resistance.

PRODUCTION EXAMPLE 8

The epoxidizing reaction was carried out in the same manner as in Example 1 except that the bisphenol was replaced by 202 g of bishenol obtained in the above-mentioned Production Example 7. 284 g of light yellow solid having an epoxy equivalent of 278 and a softening point of 62° to 67° C. was obtained.

uct solution was allowed to stand at room temperature for 2 hours to precipitate and crystallize the desired product, 3,9-bis[p-(2,3-epoxypropoxy)phenyl]-2,4,8,10-tetraoxaspiro[5,5]undecane. The unreacted epichlorohydrin was recovered by filtration and the desired product was washed with water using a mixer to completely remove salts by-produced. Recrystallization was conducted using dioxane to obtain 201.1 g of white crystal (yield: 88.2%).

The crystal has a melting point of 175° to 176° C. and an epoxy equivalent of 228 which was equal to the theoretical epoxy equivalent value of 228.

EXAMPLE 4

Into a 500 ml four-necked flask equipped with a thermometer, stirrer, nitrogen inlet and condenser were charged 37.4 g of bisphenol obtained in Production Example 1 and 252.0 g of the epoxy compound obtained in Example 1 and the mixture was heat melted at 180° C. in an oil bath under nitrogen stream. 2600 ppm of ammonium tetramethyl chloride per epoxy was added thereto and reaction was conducted for 30 minutes. The polyepoxy compound obtained was a light yellow solid and had a softening point of 79° to 91° C., epoxy equivalent of 333 and molecular weight measured by Gel Permeation Chromatograph (polystyrene standard sample calculated value) of 1,270.

EXAMPLE 5

Example 4 was repeated except that the amount of bisphenol was changed to 74.8 g (equivalent ratio 0.4) to obtain a polyepoxy compound having a softening point of 104° to 124° C., epoxy equivalent of 463 and molecular weight of 1,600.

EXAMPLE 6

Example 4 was repeated except that the bisphenol was replaced by 48.4 g (0.4 equivalent) of 3,3',5,5'-tetramethyl-4,4'-hydroxybiphenyl to obtain a polyepoxy compound having a softening point of 110° to 131° C., epoxy equivalent of 501 and molecular weight of 1,550.

EXAMPLE 7

Example 4 was repeated except that the bisphenol was replaced by 60.6 g (0.3 equivalent) of bisphenol obtained in Production Example 4 to obtain a polyepoxy compound having a softening point of 96° to 115° C., epoxy equivalent of 433 and molecular weight of 1,370.

EXAMPLE 8

Example 4 was repeated except that the bisphenol was replaced by 68.8 g (0.4 equivalent) of bisphenol obtained in Production Example 7 to obtain a polyepoxy compound having a softening point of 118° to 130° C., epoxy equivalent of 450 and molecular weight of 1,400.

EXAMPLE 9

Example 5 was repeated except that the epoxy compound was replaced by 284 g (0.4 equivalent) of an epoxy compound obtained in Production Example 8 to obtain a polyepoxy compound having a softening point of 110° to 131° C., epoxy equivalent of 501 and molecular weight of 1,550.

EXAMPLE 10

Example 5 was repeated except that the epoxy compound was replaced by 228 g (0.4 equivalent) of an epoxy compound obtained in Production Example 9 to obtain a polyepoxy compound having a softening point of 108° to 130° C., epoxy equivalent of 422 and molecular weight of 1,440.

APPLICATION EXAMPLES 100 parts by weight of each of polyglycidyl ethers obtained in Examples 4 to 10 was blended with an equivalent of diaminodiphenyl sulfone (hardener). After deaeration treatment for 10 minutes under a reduced pressure of 1.0 mmHg, the mixture was cast into a metallic mold. Precuring was carried out at 180° C. for 1 hour and postcuring was carried out at 190° C. for 4 hours to obtain cured products having the physical properties shown in Table 4 below.

Test Method
Heat distortion temperature: ASTM D-648,
Flexural strength: JIS K-6911,
Flexural modulus: JIS K-6911,
Tensile strength: JIS K-6911.

TABLE 4

| | Application Examples | | | | | | | | Referential Examples | | |
|---|---|---|---|---|---|---|---|---|---|---|---|
| Composition (parts by weight): | | | | | | | | | | | |
| Polyglycidyl ether | 100 (Example 4) | 100 (Example 5) | 100 (Example 6) | 100 (Example 7) | 100 (Example 8) | 100 (Example 9) | 100 (Example 10) | 100 (Example 1) | 100 (Production Example 1) | 100 (Production Example 4) | 100 Epikote 828 |
| 4,4'-Diaminodiphenylsulfone | 18.6 | 13.4 | 12.4 | 14.3 | 13.8 | 11.9 | 14.7 | 22.1 | 22.3 | 27.2 | 32.6 |
| Properties of cured product: | | | | | | | | | | | |
| Heat distortion temperature (°C.) | 202 | 192 | 195 | 204 | 190 | 181 | 195 | 210 | 188 | 214 | 191 |
| Flexural strength (kg/mm²) | 1,050 | 870 | 890 | 920 | 970 | 1,080 | 840 | 1,120 | 1,180 | 1,300 | 1,260 |
| Flexural modulus (kg/mm²) | 30,000 | 28,000 | 29,500 | 28,800 | 27,000 | 33,000 | 28,000 | 35,000 | 34,000 | 37,000 | 28,600 |
| Izod impact strength (notched) (kg · cm/cm) | 5.3 | 6.0 | 5.5 | 5.0 | 6.1 | 5.9 | 4.9 | 4.3 | 3.4 | 3.9 | 2.4 |
| Tensile strength (kg/mm²) | 820 | 800 | 770 | 910 | 700 | 760 | 810 | 880 | 920 | 1,000 | 760 |
| Tensile modulus (kg/mm²) | 39,000 | 31,000 | 28,000 | 32,200 | 25,500 | 28,500 | 31,500 | 53,000 | 34,000 | 32,000 | 19,700 |
| Tensile elongation (%) | 7.4 | 10.0 | 8.8 | 7.9 | 10.5 | 8.9 | 6.6 | 5.9 | 4.9 | 4.9 | 2.8 |

While the invention has been described in detail and with reference to specific embodiments thereof, it will be apparent to one skilled in the art that various changes and modifications can be made therein without departing from the spirit and scope thereof.

What is claimed is:

1. A polyglycidyl ether which is produced by reacting a mixture of 4-oxy-3-methoxybenzaldehyde and 4-oxybenzaldehyde in a molar ratio of 5/95 to 95/5 with pentaerythritol to give a bisphenol having a spiroacetal ring, and further reacting the bisphenol thus produced with epihalohydrin or β-methylepihalohydrin.

2. The polyglycidyl ether as claimed in claim 1, wherein the bisphenol is a mixture of bisphenols represented by the formulae (I) to (III)

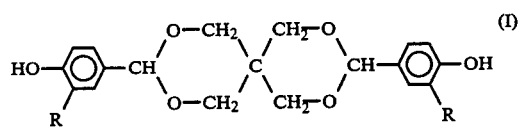

-continued

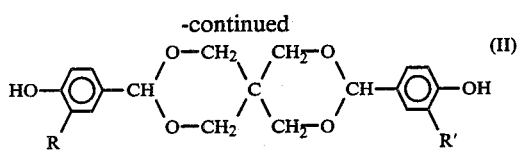
(II)

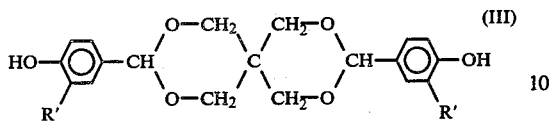
(III)

wherein R is hydrogen and R' is a methoxy group.

3. The polyglycidyl ether as claimed in claim 1, wherein the polyglycidyl ether is a diglycidyl ether represented by the formula -continued

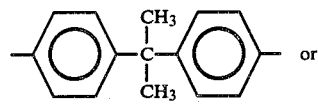
or

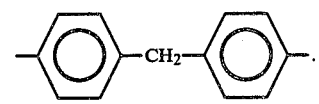

4. The polyglycidyl ether as claimed in claim 3, wherein the equivalent ratio of bisphenol to diglycidyl ether is 0.01/1 to 1/1.

5. The polyglycidyl ether as claimed in claim 4,

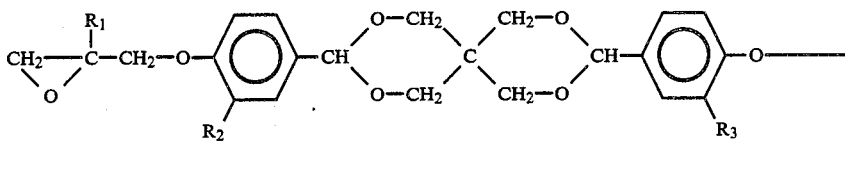

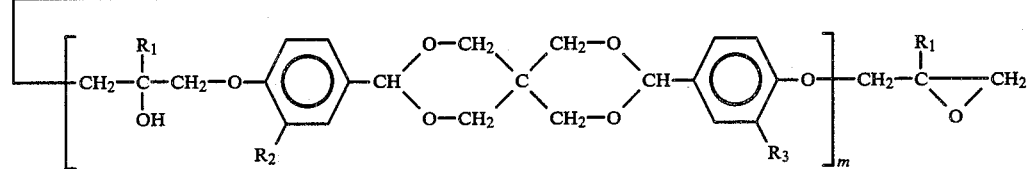

wherein $R_1$ is H or $CH_3$, $R_2$ and $R_3$ are independently hydrogen or a methoxy group, and m is 0 to 1, and the diglycidyl ether is further reacted with a bisphenol represented by the formula HO—Ar—OH wherein Ar is

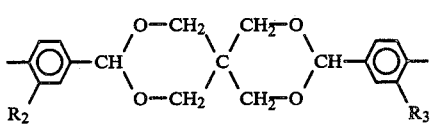

wherein $R_2$ and $R_3$ are independently hydrogen or a methoxy group,

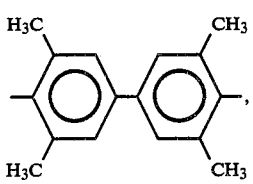

wherein the equivalent ratio is 0.05/1 to 0.8/1.

6. The polyglycidyl ether as claimed in claim 1, wherein said mixture has a molar ratio of 20–80 mole percent of 4-oxy-3-methoxybenzaldehyde and 80–20 mole percent of 4-oxybenzaldehyde.

7. The polyglycidyl ether as claimed in claim 1, wherein the reaction between the bisphenol and the epihalohydrin or said β-methylepihalohydrin is further effected first in the presence of a catalyst selected from the group consisting of a phosphonium salt or a quaternary ammonium salt, and then an alkali metal hydroxide is added.

8. The polyglycidyl ether as claimed in claim 7, wherein said catalyst is tetramethylammonium chloride or tetraethylammonium bromide.

9. The polyglycidyl ether as claimed in claim 1, wherein the reaction between said bisphenol and said epihalohydrin or said β-methylepihalohydrin is further effected in the presence of an alkali metal hydroxide.

10. A polyglycidyl ether having the formula:

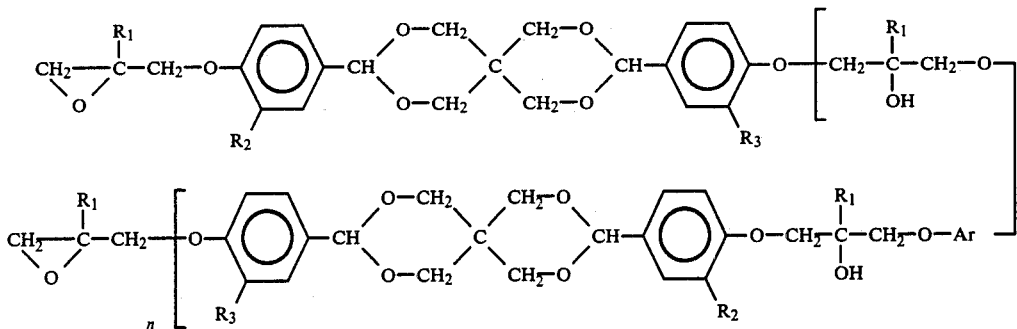

wherein $R_1$ is H or $CH_3$, $R_2$ and $R_3$ are independently hydrogen or a methoxy group, but are not simultaneously hydrogen or a methoxy group, n is 0 or an integer of 1 to 20, which is produced by reacting a diglycidyl ether of the formula:

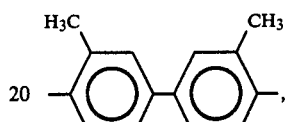

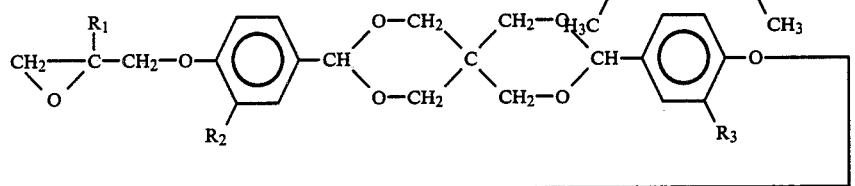

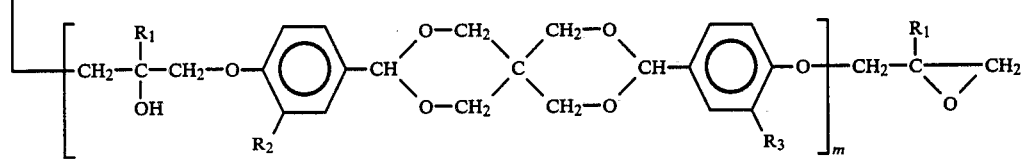

wherein $R_1$, $R_2$ and $R_3$ are as defined above, and m is 0 or 1, with a bisphenol having the formula:

HO—Ar—OH wherein Ar is:

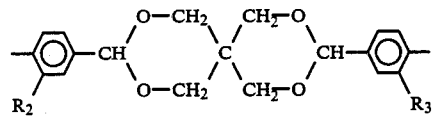

wherein $R_2$ and $R_3$ are as defined above or are selected from the group consisting of:

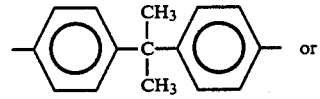

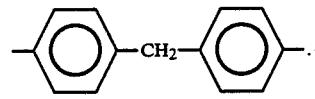

11. The polyglycidyl ether as claimed in claim 10, wherein the methoxy group content is 5-95%.

* * * * *